United States Patent
Calias et al.

(10) Patent No.: US 7,189,413 B2
(45) Date of Patent: Mar. 13, 2007

(54) DRUG DELIVERY OF PROTEINS FROM POLYMERIC BLENDS

(75) Inventors: Pericles Calias, East Boston, MA (US); Robert J. Miller, East Sandwich, MA (US); James R. Olson, Norwich, CT (US)

(73) Assignee: Genzyme Corporation, Cambridge, MA (US)

( * ) Notice: Subject to any disclaimer, the term of this patent is extended or adjusted under 35 U.S.C. 154(b) by 576 days.

(21) Appl. No.: 10/075,184

(22) Filed: Feb. 14, 2002

(65) Prior Publication Data

US 2002/0182254 A1 Dec. 5, 2002

Related U.S. Application Data

(63) Continuation of application No. 09/063,098, filed on Apr. 20, 1998, now abandoned.

(51) Int. Cl.
*A61K 9/10* (2006.01)
*A61K 47/44* (2006.01)
*A61K 47/34* (2006.01)

(52) U.S. Cl. .................. 424/486; 514/772.7; 514/786; 514/787

(58) Field of Classification Search ................ 424/486, 424/457, 466, 426, 428, 501; 514/955, 960, 514/963, 772.7, 786–787

See application file for complete search history.

(56) References Cited

U.S. PATENT DOCUMENTS

| | | | |
|---|---|---|---|
| 2,576,576 A | 11/1951 | Cresswell et al. | |
| 3,896,814 A | 7/1975 | Vivien et al. | |
| 4,137,279 A | 1/1979 | Smith et al. | |
| 4,201,216 A | 5/1980 | Mattei | |
| 4,624,256 A | 11/1986 | Messier et al. | |
| 4,649,920 A | 3/1987 | Rhum | |
| 4,786,501 A | * 11/1988 | Janski et al. | |
| 5,084,267 A | * 1/1992 | Damani | |
| 5,278,201 A | * 1/1994 | Dunn et al. | |
| 5,378,540 A | 1/1995 | Olson | |
| 5,380,780 A | 1/1995 | Olson | |
| 5,610,214 A | 3/1997 | Olson | |
| 5,641,502 A | * 6/1997 | Skalla et al. | |
| 5,741,600 A | 4/1998 | Olson | |

OTHER PUBLICATIONS

A.M. Klibanov et al., "A New Approach to Preparative Enzymatic Synthesis"; Biotechnology & Bioengineering, vol. XIX, pp. 1351-1361 (1977) by John Wiley & Sons, Inc.

"Final Report on the Safety Assessment of Blyceryl Sterate and Glyceryl Stearate/SE": J. Am. College Toxicology, vol. 1, No. 4, 12982, pp. 169-192 (1982).

Rong-Kun Chang, James C. Price and Clyde W. Whitworth, "Control of Drug Release Rates Through the Use of Mixtures of Polycaprolactone and Cellulose Propionate Polymers"; *Pharm Technol.*, pp. 24-33, Oct. 1986.

Chang et al., "Control of Drug Release Rate by Use of Mixtures of Polycaprolactone and Cellulose Acetate Butyrate Polymers"; Drug Dev. & Indus. Pharmacy, 13(6), 1119-1135 (1987).

J. Heller, "Synthesis and Use of Poly (Ortho Esters) for the Controlled Delivery of Therapeutic Agents"; Technomic Pub. Co. Inc. 1988, J. Bioactive and Compatible Polymers, vol. 3, Apr. 1988, pp. 97-105.

C.G. Pitt et al., "Aliphatic Polyesters. 1. The Degradation of Poly(E-Caprolactone) In vivo"; Journal of Applied Polymer Science, vol. 26, 3779-3787 (1981).

* cited by examiner

*Primary Examiner*—Edward J. Webman
(74) *Attorney, Agent, or Firm*—Cohen, Pontani, Lieberman & Pavane

(57) ABSTRACT

Degradable blend of polycaprolactone and crystallization modifier especially suitable for use in the controlled release of biologically active proteins

23 Claims, 2 Drawing Sheets

LUPROLIDE ACETATE DISSOLUTION

DRUG DELIVERY OF PROTEINS FROM POLYMERIC BLENDS

This is a continuation of application Ser. No. 09/063,098 filed Apr. 20, 1998 now abandoned.

BACKGROUND OF THE INVENTION

1. Field of the Invention

The present invention pertains generally to degradable blends for drug delivery systems. More particularly, the invention relates to degradable compositions which include a homopolymer of ε-caprolactone, a crystallization modifier, and a biologically active drug.

2. Description of the Related Art

During the past thirty years, the use of synthetic degradable or absorbable polymers in medical devices and drug delivery systems has made a dramatic rise. Foremost in the area of absorbable medical devices has been the usage of absorbable polyesters that are usually aliphatic and linear. For example, in the area of wound closure, there has been extensive application of the homopolymer poly(glycolic acid), see for example U.S. Pat. No. 3,297,033, and copolymers of glycolic acid with a variety of other monomers which produce likewise absorbable polymers, see for example U.S. Pat. No. 3,839,297.

Dependent upon the specific application, there is a preferred time window where the synthetic polymer has been completely absorbed or degraded, that is, has lost all of its mass to the surrounding tissue. In the case of absorbable sutures in sewn tissue after surgery, that window is usually within one year, although even shorter times are more preferable (U.S. Pat. Nos. 4,027,676 and 4,201,216). For other applications such as drug delivery systems this time window could be either shorter or longer. Thus, for a given application there is a need to use absorbable polymers that degrade within the time limits of that application.

There is some leeway in the selection of synthetic absorbable polyesters for a given application since the rates of the hydrolysis of this class of polymers do vary over a wide range. Differences in the rates of hydrolysis of absorbable synthetic polyesters can be attributed to the intrinsic hydrolytic stability of their specific ester linkages and to the physical properties of their respective polymers. For instance, the hydrolytic stability of the ester linkage is strongly influenced by both electronic and steric factors. An example of an electronic effect is the increased reactivity of ester linkages which have a hydroxy substitution α to the ester linkage, as in the case of esters of glycolic acid. Physical properties which are important to the hydrolytic behavior and subsequent mass loss in synthetic absorbable polyesters include the glass transition temperature and the degree of crystallization in the polymer. In semi-crystalline polymers link poly(glycolic acid) and polycaprolactone, it has been hypothesized that hydrolysis takes place initially in the amorphous areas of the polymer, where migration or absorption of the water molecule is facile compared to the crystalline areas. Thus it appears that the water molecule prior to reaction at an ester linkage of a synthetic absorbable polyester must first have access or absorption into the polymer. Crystalline areas of the polymer have been hypothesized to impede the access or penetration of water molecules. Therefore, to the extent that this takes place, the overall hydrolytic breakdown of the absorbable polyester is retarded. In the case of polycaprolactone, the hydrolytic degradation rate and subsequent mass also is also dependent upon particle size, wherein small particles degrade and lose mass much more rapidly than a polymer cast in film form.

In the specific application of drug delivery systems, one major concern is that the use of synthetic polymer blends with biologically active proteins would inactive the proteins. Proteins may be incorporated by polymer blends by dissolving the protein and blend in an organic solvent and then casting from solution. However, proteins are known to inactivate in the presence of organic solvents. For example, proteins generally have decreased thermal stability in the presence of organic solvents, see L. Lee et al. *Biochemistry*, pages 7813–7819 (1987). As a further example, enzymes are known to function effectively only in aqueous solution and become unstable and catalytically inactive in the presence of organic solvents.

It is thought that, in organic solvents, enzymes change their conformation and as a consequence decrease their catalytic potential, see for example A. M. Klibanov et al. *Biotechnology and Bioengineering* vol XIX, pages 1351–1361 (1977).

Accordingly, an object of the invention is to provide a polymeric blend that can be mixed with a protein without inactivating the biological activity of the protein during mixing, while the protein is held within the polymeric blend or during controlled release of the protein.

A further object of the invention is to provide a controlled degradable matrix for the controlled in vivo release of biologically active proteins.

SUMMARY OF THE INVENTION

The present invention is directed toward a preparation that provides extended release of a biologically active protein comprising an effective amount of the protein in a degradable blend comprising a homopolymer of ε-caprolactone and a crystallization modifier. The protein of the present invention generally includes enzymes, peptides and antibobies. The crystallization modifier might be either a crystalline fatty acid or a crystalline ester of a fatty acid. Preferably, the crystallization modifier is a crystalline ester of a fatty acid. Particularly suitable crystallization modifiers are crystalline ester of fatty acids which are saturated $C_{12}$–$C_{18}$ fatty acid esters of polyhydric alcohols. Preferably, the polyhydric alcohols might be glycerol, ethylene glycol or propylene glycol. Most preferably, the polyhydric alcohol is glycerol monostearate.

The blend composition includes a range from about 95 to about 5% by weight of the homopolymer of ε-caprolactone and a range of from about 5 to about 95% by weight of the crystallization modifier. In one blend composition, the homopolymer of ε-caprolactone ranges form about 70 to about 30% by weight and the crystallization modifier ranges in weight from about 30 to about 70%. In a specific blend composition, the homopolymer of ε-caprolactone and the crystallization modifier are each about 50% by weight. The homopolymer of ε-caprolactone has a molecular weight of at least about 1,000 and a molecular weight range of preferably from about 15,000 to about 100,000. The protein is added to the blend in the amount ranging from about 1% to about 60%, preferably about 10% to about 40%, by weight of the blend. The protein may be added in solid form or in liquid form, preferably in a lyophilized powder form.

The invention further embodies a method for affecting the rate of release of biologically active protein by affecting the rate of degradation of polycaprolactone comprising the step of blending a homopolymer of ε-caprolactone, a crystallization modifier and the biologically active protein. The amount of each component is the same as discussed above for the preparation. The degradation rate increases as the blend ratio of the crystallization modifier to the homopolymer of ε-caprolactone increases. An increase in degradation rate increases the rate of release of the protein.

DETAILED DESCRIPTION OF THE PRESENTLY PREFERRED EMBODIMENTS

Figure 1:
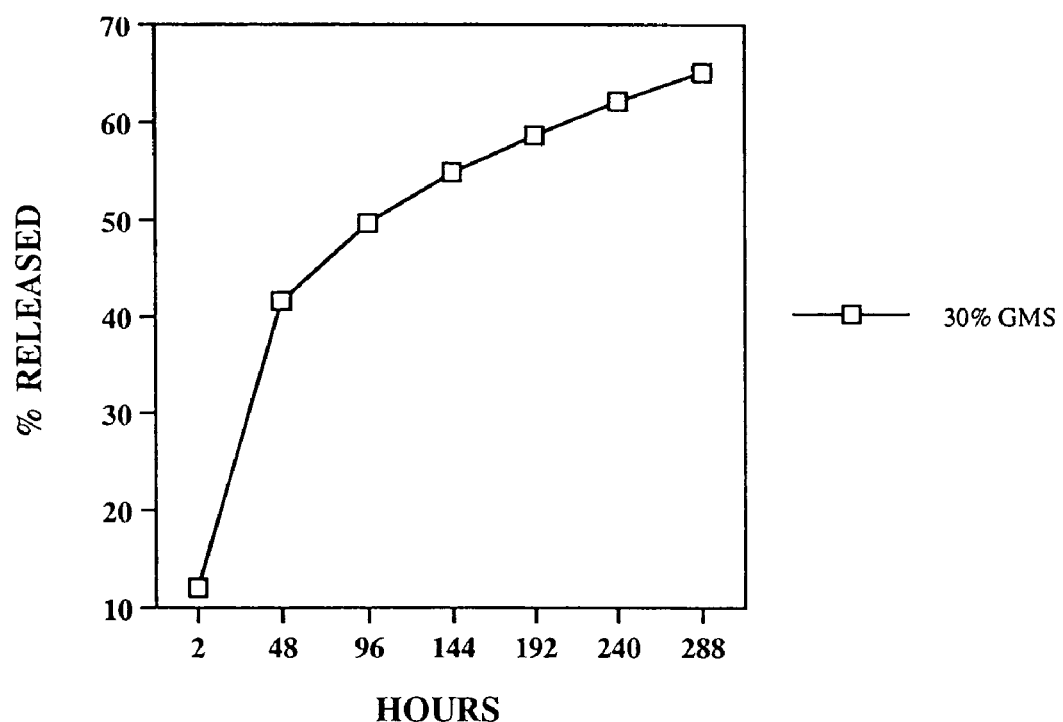
FIG. 1 shows the rate of release of leuprolide acetate from a blend of polycaprolactone and glycerol monostearate.

The in vivo degradation rate of polycaprolactone can be increased by blending the polymer with crystalline fatty acid esters of polyhydric alcohols, which function as crystallization modifiers. Furthermore, the rate of this degradation can be regulated by control of the amount of added crystalline modifier. These blends can be used in the controlled release of chemical, pharmaceutical or biological agents.

The rate of hydrolysis and subsequent mass loss in the hydrolytic degradation of polycaprolactone has been increased through the blending of the polycaprolactone with a crystallization modifier. In essence, the crystallization modifiers have been found to reduce the amount of crystallization in the polycaprolactone and to also retard the film forming ability of polycaprolactone that has been cast from solution in a volatile solvent or by a melt blend. Remarkably, the blending of the polycaprolactone with the crystallization modifiers of the present invention does not adversely affect the desired properties of the polycaprolactone. The crystallization modifiers of the present invention are themselves crystalline in nature and readily form homogeneous solid blends with polycaprolactone either by casting from a solution of each or by preparation from a melt. This suggests an interaction and compatibility between the polycaprolactone and the non-polymer crystallization modifiers.

In this invention, both homopolymers and copolymers of ε-caprolactone are suitable for blending with a crystallization modifier. Homopolymer of ε-caprolactone should have a minimum molecular weight of at least about 1000. However, there is no maximum limit that is applicable to the homopolymer. A variety of molecular weights in polycaprolactones is commercially available from Union Carbide Corporation under the Tone brand name. For example, lower molecular weight polycaprolactones are available as Tone Polyols, while higher molecular weight polycaprolactones are available as Tone PCL-300, Tone PCL-700 and PCL-767E which have weight average molecular weights of 15,000, 40,000 and 76,000 respectively, as reported by the manufacturer. Copolymers of ε-caprolactone are those synthesized from at least about 80% by weight of the ε-caprolactone monomer and the corresponding remainder of another absorbable monomer. The copolymers could be either random or block copolymers. Absorbable monomers consistent with these copolymers include glycolic acid, lactic acid, and other aliphatic hydroxycarboxylic acids which are usually polymerized from their corresponding lactones, that is, glycolide, lactide, etc. Such copolymers, which contain a high percentage by weight of polycaprolactone segments, can have their in vivo degradation rates increased by their blending with crystallization modifiers.

In this invention, crystallization modifiers have been found which affect the crystallinity of polycaprolactone and its film forming ability. The preferred crystallization modifiers have been found to be saturated $C_{12}$–$C_{18}$ fatty acid esters of polyhydric alcohols. Polyhydric alcohols useful in this invention are, for example, glycerol, ethylene glycol and propylene glycol. Commercial sources of these materials, which are often a mixture of compounds like glycerol monostearate (also contains glycerol palminate for instance), are suitable in this invention. Such esters are crystalline in nature, that is, show characteristic X-ray powder diffraction patterns of crystalline matter. It is believed that this inherent crystallinity of these fatty acid esters allows for a crystalline interaction with the "semi-crystalline" polycaprolactone, which produces a lower net crystallinity in the blend. Furthermore, that this disruption in crystallinity in the net blend and in the constituent polycaprolactone is responsible for the disruption in film forming ability in the polycaprolactone. Thus, two factors of critical importance in the rate of hydrolytic degradation and subsequent mass loss of polycaprolactone can be controlled by the addition of the crystallization modifiers of this invention. Another important characteristic of these crystallization modifiers is that they are water insoluble, but enzymatically degradable. Therefore, the crystallization modifiers will not be rapidly leached out of their crystalline interaction with the polycaprolactone and can prevent the re-crystallization of the polycaprolactone as it is subject to hydrolytic degradation.

X-ray powder diffraction spectra have been taken on polycaprolactone-700 (PCL-700) (Union Carbide), glycerol monostearate (GMS) pure (Stepan Chemical Co.), physical mixtures of the two components, and blends of the two components. The physical mixture of the two components was prepared by mixing equal amounts of powdered PCL-700 and GMS together at room temperature. The blends were prepared for the diffraction experiments by first dissolving the two solutes in a methylene chloride/methanol solvent to give about a 10% by weight solution. Next, the solvent was evaporated to leave the solid blend, which was carefully ground with a mortar and pestle to produce uniform powder. Diffraction patterns were recorded in the range of 2θ values of 100 to 300 with a powder diffractometer using copper Kα radiation. Maximum diffraction intensities were observed in this range for the polycaprolactone, the glycerol monostearate, the physical mixture, and the respective blends. The total area underneath each diffraction pattern was quantified, then scaled to a relative area based upon the physical mixture having an area value of 100. The relative area for each sample is a measure of its total crystallinity. A comparison of the relative areas under the diffraction patterns in this range is give in Table 1.

TABLE 1

| COMPOSITION | RELATIVE AREA | % DECREASE IN TOTAL CRYSTALLINITY |
|---|---|---|
| Physical mixture 50% PCL + 50% GMS | 100 | — |
| Blend 50% PCL + 50% GMS | 65 | 35% |
| Blend 33% PCL + 67% GMS | 56 | 44% |

TABLE 1-continued

| COMPOSITION | RELATIVE AREA | % DECREASE IN TOTAL CRYSTALLINITY |
|---|---|---|
| Blend 20% PCL + 80% GMS | 45 | 55% |

Comparison of the diffraction pattern of a 1 to 1 physical mixture of polycaprolactone (PCL) with glycerol monostearate (GMS) to the diffraction pattern of the 1 to 1 blend of the two component, which was prepared as described above, shows a 35% decrease in crystallinity in the blend. Larger decreases in crystallinity occur as the proportion of the glycerol monostearate is increased. Furthermore, it is evident that the crystallinity is decreased in both components. Thus, an intimate interaction between the two components is suggested.

A qualitative assessment of the relative film forming ability of polycaprolactone versus the blends of this invention was carried out by decantation of the respective 10% by weight solutions onto a flat surface and allowing the solvent to evaporate. In this experiment mono-di-glycerides (MDG) (Stepan Chemical Co.) was used as the crystallization modifier for polycaprolactone-700 (Union Carbide). These results are summarized in Table II and show a dramatic decrease in film forming ability as the proportion of the crystallization modifier is increased.

TABLE II

| COMPOSITION | FILM DESCRIPTION |
|---|---|
| 100% PCL | strong, tough, clear |
| 90% PCL + 10% MDG | very weak film, opaque |
| 70% PCL + 30% MDG | forms white layer, weak cohesion |
| 50% PCL + 50% MDG | forms white solid, weak cohesion |
| 30% PCL + 70% MDG | forms white particulate solid |
| 10% PCL + 90% MDG | forms white particulate solid |

The film forming tendencies of the blends of this invention were further investigated by following coated poly (glycolic) (PGA) suture integrity under in vitro conditions. For example, size 0 braided poly(glycolic acid) sutures uncoated, with 100% polycaprolactone-700 (Union Carbide), and coated with a 1 to 1 blend of polycaprolactone-700 (Union Carbide) and glycerol monostearate pure (Stepan Chemical Co.) were each immersed in buffer solution at a pH of 7.0 in test tubes and placed in a constant temperature bath at 50° C. The coated sutures had coating weight pick-ups of 7 and 5% for the PCL-700 and the 1 to 1 blend, respectively. Visual inspection of the sutures was recorded over time. By Day-48 both the uncoated PGA suture and the suture coated with a blend of PCL/OMS had degraded to a lint-like residue. However, the PCL coated suture was only broken into small rigid segments. This appearance of the PCL coated suture was unchanged at Day-78 and suggested that the suture was encapsulated by a strong, tough film of the polycaprolactone. On the other hand, both the uncoated suture and the suture coated with a 1 to 1 blend of PCL/GMS exhibited a similar degree of degradation in the same time frame of 48 days.

The blends of polycaprolactone and crystallization modifiers of the present invention have application in the controlled release of biologically active proteins. Indeed, the proportion of crystallization modifier to polycaprolactone can be used to regulate the rate of release of the proteins. Moreover, these blends have improved rates of mass loss when compared to matrices of 100% PCL. The blending of polycaprolactone with a crystallization modifier like glycerol monostearate thus produces an absorbable matrix with many beneficial attributes. Besides the benefit of regulated release and mass loss, blends of this invention are expected to in general release proteins faster than that of 100% polycaprolactone, yet much slower than 100% of crystallization modifier like glycerol monostearate.

The following illustrate, by way of example, use of an absorbable blend for an absorbable controlled release matrix.

EXAMPLE 1

The following example illustrates the controlled release of a peptide, leuprolide acetate. Leuprolide acetate is a non-aopeptide LH-RH agonist (for a review see: Adjei, A. L.; and HSU, L. in *Stability and Characterization of Protein and Peptide Drugs: Case Histories*, edited by John Wang and Rodney Pearlman, Plenum Press, New York, 1993, pages 159–199).

3.85 gm of polycaprolactone and 1.65 gm of glycerol monostearate were melt mixed at 80° C. for 30 mm. at which point 547 mg of leuprolide acetate was added and the mixture stirred at 80° C. for an additional 5 mm. The mixture was cooled to room temperature. The mixture was then melted into a cylindrical shape, cooled to 4° C. and cut into disk shaped pellets (diameter=4.6 mm, width=≈2 mm). About 34 mg of the pellets were then placed into a capped vial containing 10 mL phosphate buffered solution (PBS) (containing 0.1% $NaN_3$). The dissolution was placed at 37° C. on an orbital shaker revolving at approximately 162 rpm.

The release of leuprolide acetate from the pellets was measured over time using an isocratic, stability-indicating HPLC assay. The method has been validated for specificity, linearity, precision, accuracy, limit of quantitation, limit of detection, and ruggedness. The method employed a C18 (USP type L1) HPLC column with a mobile phase of 179.4/770. (w/w) acetonitrile/95 mM sodium phosphate buffer (pH 6.5). The flow rate is 1.5 mL/min. Peak detection is performed using a single wavelength UV detector with a wavelength switching capability. A wavelength of 254 nm is used for the first five minutes and then switched to 220 nm for the remainder of the analysis.

The rate of release of leuprolide acetate is shown in FIG. 1.

EXAMPLE 2

The following example illustrates the stability of an antibody, Anti-EM, when incorporated in the polymer blend of the present invention. Anti-Em is an $IgG_1$ mouse monoclonal antibody specific for Human Red Cell Antigen. A 500 ml solution of an antibody, Anti-EM, was dialyzed against deionized water with a 12,000–14,000 molecular weight cut off for 24 hours, the solution was then lyophilized over 3 days. 20 g of glycerol monostearate and 20 g of polycaprolactone were melt mixed at 90° C. for 2 minutes to 20 minutes with 1.9 g of the lyophilized powder of anti-EM. Melt mixing was conducted for two minutes. The melt was left standing at 90° C. for an additional minute. The melt was then placed in a freezer at –20° C. for about five minutes. A plug of pellet was punched out and left at 4° C. for about one hour. The pellet has a diameter 11.4 mm and width =3 mm. About 300 mg of pellets were placed into a capped vial containing 2 mL of phosphate buffered solution that contains 0.1% $NaN_3$. The vial was agitated by vortex for 15 minutes.

The antibody that was dissolved in the aqueous phase was analyzed by flow cytometry using the degree of degradation of light at a wavelength of 280nm to determine the concentration of active antibody. The results of the flow cytometry analysis indicate that the antibody, anti-EM, remained active after melt mixing for up to 20 minutes at 90° C.

Based on the above study, controlled release of the antibody, anti-EM, from a blend of glycerol monostearate and polycaprolactone is possible.

EXAMPLE 3

The following example illustrates the controlled release of an enzyme, alkaline phosphatase, from a polymer blend of the present invention. The pellets were made as in the leuprolide acetate Example 1 with the following exceptions:

| | |
|---|---|
| 7.0 g | polycaprolactone |
| 3.0 g | glycerol monostearate |
| 1.0 g | Alkaline Phosphate |

(Sigma # p-764O Lot # 75H7051)

About 32 mg of the pellets were placed into a capped vial containing 10 mL phosphate buffered solution (PBS) (containing 0.1% $NaN_3$). The dissolution was placed at 37° C. on an orbital shaker revolving at approximately 162 rpm. An ELISA assay was used to determine active material, and both amino acid analysis and A 280 were used to determine total protein content.

Figure 2:
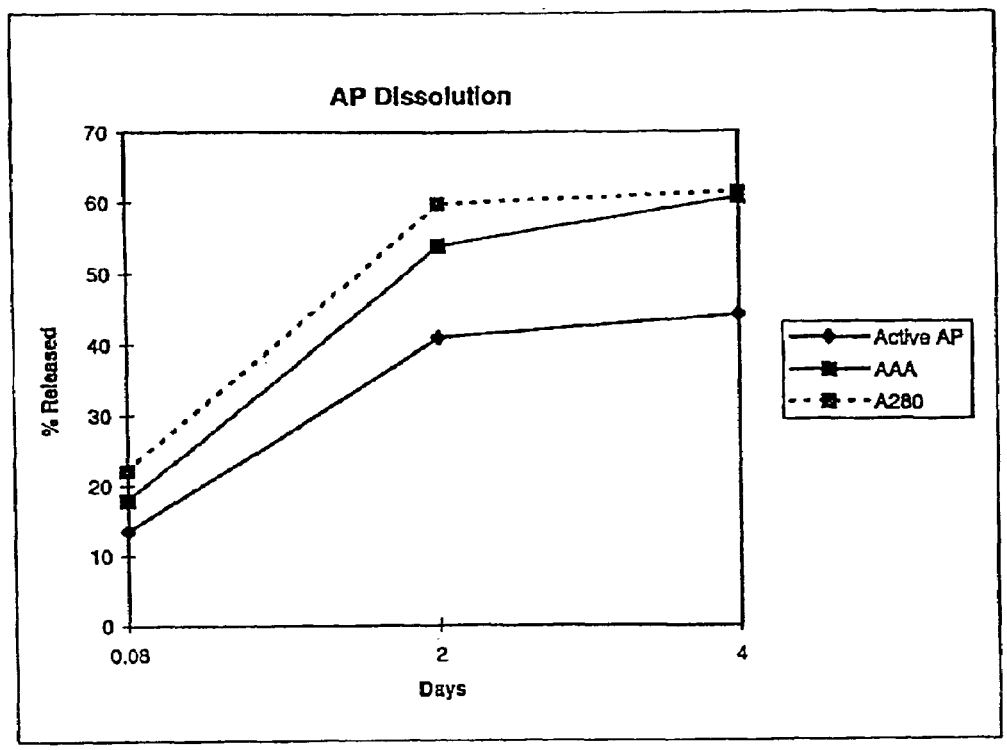
FIG. 2 shows the rate of release of alkaline phosphatase from a blend of polycaprolactone and glycerol monostearate. The released alkaline phosphatase is measured in terms of active phosphate, and total protein content by amino acid analysis and A280.

Results of the dissolution study are shown in FIG. 2 and indicate that 60% of the alkaline phosphatase was released in four days. About 66.6% of the alkaline phosphatase that was released was biologically active.

The present invention has been described herein with specific reference to the preferred embodiments thereof. However, those skilled in the art will understand that changes may be made in the form of the invention covered by the claims without departing from the scope and spirit thereof, and that certain features of the invention may sometimes be used to an advantage without corresponding use of the other features. All references cited herein are incorporated by reference in their entireties.

We claim:

1. A method for controlling the rate of release of a biologically active protein within a living organism comprising the step of administering a biodegradable preparation, wherein the biodegradable preparation comprises the protein in a biodegradable blend of about 95 to 5% by weight of a homopolymer of ε-caprolactone and about 5 to about 95% by weight of a crystallization modifier selected from the group consisting of crystalline fatty acids and crystalline esters of fatty acids that are saturated $C_{12}$–$C_{18}$ fatty acid esters of polyhydric alcohols; and wherein the biodegradable preparations is in solid form outside the living organism.

2. The method of claim 1 wherein the crystallization modifier is crystalline esters of fatty acids that are saturated $C_{12}$–$C_{18}$ fatty acid esters of polyhydric alcohols.

3. The method of claim 2 wherein the polyhydric alcohols are selected from the group consisting of glycerol, ethylene glycol and propylene glycol.

4. The method of claim 3 wherein the polyhydric alcohol is glycerol monostearate.

5. The method of claim 1 wherein the protein is selected from the group consisting of enzyme, peptide and antibody.

6. The method of claim 1 further comprising lyophilizing a solution containing the protein before adding the protein to the blend.

7. The method of claim 1 wherein the protein is added in the amount ranging from about 1% to about 60% by weight of the blend.

8. The method of claim 7 wherein the protein is added in the amount ranging from about 10% to about 40% by weight of the blend.

9. A method for controlling the rate of release of a biologically active protein within a living organism comprising the step of administering a biodegradable preparation, wherein the biodegradable preparation comprises the protein in a biodegradable blend of about 95 to 5% by weight of a copolymer of at least 80% by weight ε-caprolactone and corresponding remainder weight of another absorbable monomer; and about 5 to about 95% by weight of a crystallization modifier selected from the group consisting of crystalline fatty acids and crystalline esters of fatty acids that are saturated $C_{12}$–$C_{18}$ fatty acid esters of polyhydric alcohols; and wherein the biodegradable preparation is in solid form outside the living organism.

10. A biodegradable preparation providing extended release of a biologically active protein within a living organism comprising an effective amount of the protein in a blend of about 95 to 5% by weight of a homopolymer of ε-caprolactone and about 5 to about 95% by weight of a crystallization modifier selected from the group consisting of crystalline fatty acids and crystalline esters of fatty acids that are saturated $C_{12}$–$C_{18}$ fatty acid esters of polyhydric alcohols; wherein the biodegradable preparation is in solid form outside the living organism.

11. The preparation of claim 10 wherein the protein is an enzyme.

12. The preparation of claim 11 wherein the enzyme is alkaline phosphatase.

13. The preparation of claim 10 wherein the protein is a peptid.

14. The preparation of claim 13 wherein the peptide is leuprolide acetate.

15. The preparation of claim 10 wherein the protein is an antibody.

16. The preparation of claim 15 wherein the antibody is anti-EM.

17. The preparation of claim 10 wherein the crystallization modifier is crystalline esters of fatty acids which are saturated $C_{12}$–$C_{18}$ fatty acid esters of polyhydric alcohols.

18. The preparation of claim 17 wherein the polyhdric alcohols are selected from the group consisting of glycerol, ethylene glycol and propylene glycol.

19. The preparation of claim 18 wherein the polyhydric alcohol is glycerol monostearate.

20. The preparation of claim 10 wherein the homopolymer of ε-caprolactone is present in the amount ranging from about 70% to about 30% by weight of the blend and the crystallization modifier is present in the amount ranging from about 30% to about 70% by weight of the blend.

21. The preparation of claim 20 wherein the homopolymer of ε-caprolactone and the crystallization modifier are each about 50% by weight of the blend.

22. A biodegradable preparation providing extended release of a biologically active protein within a living organism comprising an effective amount of the protein in a blend of about 95 to 5% by weight of a copolymer of at least 80% by weight of ε-caprolactone and corresponding remainder weight of another absorbable monomer; and about 5 to about 95% by weight of a crystallization modifier selected from the group consisting of crystalline fatty acids and crystalline esters of fatty acids that are saturated $C_{12}$–$C_{18}$ is fatty acid esters of polyhydric alcohols; wherein the biodegradable preparation is in solid form outside the living organism.

23. A biodegradable preparation providing extended release of a biologically active protein comprising an effective amount of the protein in a blend of about 95 to 5% by weight of a homopolymer of ϵ-caprolactone and about 5 to 95% by weight of a crystallization modifier selected from the group consisting of crystalline fatty acids and crystalline esters of fatty acids that are saturated $C_{12}$–$C_{18}$ fatty acid esters of polyhydric alcohols; wherein the homopolymer has a molecular weight range from 15,000 to 100,000.

* * * * *